United States Patent [19]

Bosley et al.

[11] 4,190,563

[45] Feb. 26, 1980

[54] PARTICULATE ABSORBANT MATERIAL SURFACE TREATED WITH POLYETHER TO IMPROVE DISPERSIBILITY IN BLOOD

[75] Inventors: John A. Bosley, Higham Ferrers; Vicki Maddison, Bedford; Alan A. McKinnon, Higham Ferrers, all of England

[73] Assignee: Lever Brothers Company, Inc., New York, N.Y.

[21] Appl. No.: 950,924

[22] Filed: Oct. 12, 1978

[30] Foreign Application Priority Data

Oct. 18, 1977 [GB] United Kingdom ............... 43308/77
Apr. 10, 1978 [GB] United Kingdom ............... 13951/78

[51] Int. Cl.$^2$ ................................................. C08L 3/02

[52] U.S. Cl. ............................... 260/17.4 GC; 128/284; 128/285; 128/290 R; 128/296; 47/DIG. 9; 260/9; 260/13

[58] Field of Search ............... 260/17.41 ST, 17.4 GC

[56] References Cited

U.S. PATENT DOCUMENTS

| 4,036,588 | 7/1977 | Williams et al. | 260/17.4 GC |
| 4,051,086 | 9/1977 | Reid | 260/17.4 GC |

*Primary Examiner*—Edward M. Woodberry
*Attorney, Agent, or Firm*—Michael J. Kelly; James J. Farrell; Melvin H. Kurtz

[57] ABSTRACT

Water-swellable particulate absorbents surface-treated with one or more polyethers containing oxyethylene and/or oxypropylene units have improved dispersibility in blood.

10 Claims, No Drawings

PARTICULATE ABSORBANT MATERIAL SURFACE TREATED WITH POLYETHER TO IMPROVE DISPERSIBILITY IN BLOOD

This invention relates to absorbent materials, more especially absorbent materials suitable for use in absorbent disposable products such as sanitary towels or napkins and tampons and absorbent products for surgical or medical use. The invention also relates to processes for producing such materials and to absorbent articles containing such materials.

In recent years there has been much interest in the synthesis of absorbent polymers having a high capacity for absorbing water and body fluids. A number of different polymers have been developed some being wholly synthetic in nature and some partially synthetic.

Among the partially synthetic absorbent polymers are those based on starch. These include the starch-acrylonitrile graft copolymers described in U.S. Pat. Nos. 3,997,484 (the USA as represented by the Secretary of Agriculture) and 3,661,815 (Grain Processing Corporation), and the cross-linked gelatinised starch derivatives described in German Patent Application No. 2702781 corresponding to copending Application No. 766,524 non abandoned and succeeded by Ser. No. 960,423 filed Nov. 13, 1978. Other examples of partially synthetic absorbent polymers are the caboxymethylated cellulose described in U.S. Patent Specification No. 3,589,364 (Buckeye Cellulose Corporation), and the carboxymethyl cellulose cross-linked by acid interestification as described by Podlas, T.J. in INDA Tech. Symp. 1976, 2–3 March, pp 25–39.

Wholly synthetic absorbents include polyacrylates crosslinked with a polyamide/epichlorhydrin material as described in German Patent Application No. 2614662 (Dow Chemical Company) and the potassium salts of polyacrylic acid cross-lined by aluminium ions as described in German Patent Application No. 2609144 (National Starch and Chemical Corporation).

The above materials are substantially water-insoluble and absorb many times their weight of water, urine or other aqueous body exudates. They retain a particulate character as they imbibe surrounding liquid and swell. In most cases, even with water, the swollen particles are gelatinous and tacky and form clusters. An exception is the cross-linked starch derivative described in German Patent Application No. 2702781, the particles of which on absorbing water are substantially non-tacky and dry to the touch. However, even this starch derivative, as well as the other absorbents previously referred to, has poor dispersibility in blood, so that when blood is brought into contact with a mass of the absorbent significant penetration into the bed and hence absorption is extremely slow. The particles have therefore what may be described as poor "blood wet-out" so that on exposure to blood the particulate material at the inside of a mass remains unreached by the blood. Although the mechanism is not understood at the present time, it appears that the blood on initial contact with the particles forms some sort of mass which acts as a barrier to the passage of the blood through the surface layers of the particles.

An object of the invention is to provide an absorbent composition having improved blood dispersibility, or "blood wet-out." It is also an object to provide a process for producing such an improved absorbent.

According to the invention there is provided a water swellable particulate absorbent material surface-treated to enhance its dispersibility in blood with one or more polyethers of the formula $$HO(C_2H_4O)_a(C_3H_6O)_b(C_2H_4O)_cH$$

where a+c represents the total number of oxyethylene units and b the number of oxypropylene units and where a+c or b may be zero, the amount of polyether being such as to permit capillary flow of blood through a mass of the particulate absorbent.

The molecular weight of the polyether is not critical and may vary for example over the range 300 to 6,000.

The polyether may be a polyoxyethylene polymer, i.e. a polyethylene glycol, in which case b in the above formula is zero. Polyethylene glycols are water-soluble. Preferred polyethylene glycols are those having a molecular weight of from 300 to 2,000.

The polyether may be a polyoxypropylene polymer, i.e. a polypropylene glycol, in which case a+c in the above formula is zero. Polypropylene glycol are not soluble in water. Preferred polypropylene glycols are those having a molecular weight of from 400 to 2,500.

The polyether may also be a water-soluble or a water-insoluble polyoxyethylene-polyoxypropylene block copolymer. By a water-soluble polyether is meant one which is soluble to the extent of more than 1% in water at 25° C., i.e. a solubility of greater than 1 g in 100 g of water. In water-soluble polyoxyethylene-polyoxypropylene copolymers the weight of the oxyethylene units exceeds about 15% by weight of the total compound. Suitable polyoxyethylene-polyoxypropylene block copolymers are those available commercially under the trade mark PLURONIC, for example the water-soluble PLURONICS L62, L43, L35 and F38, and the water-insoluble PLURONICS L61, L81, L101 and L121. Preferred polyoxyethylene-polyoxypropylene copolymers are those which are liquid at room temperature. Preferred water-soluble copolymers are those having a molecular weight of from 1,000 to 3,000.

The water swellable absorbent materials which may be treated with the polyether are exemplified by the partially synthetic and wholly synthetic absorbent polymers described above. The water retention values of such polymers are at least 2 g/g and are usually much higher. The particulate absorbent material may be in the form of a powder, granules, flakes or fibres.

The treatment of the absorbent with a liquid polyether may be effected simply by directly mixing the particulate absorbent with the polyether. When a polyether is used which is solid at normal temperature it is necessary to first melt the polyether and then to thoroughly mix the particulate absorbent with the molten polyether. Mixtures of solid and liquid polyethers would also require to the heated to melt the solid component.

The treatment of the absorbent with the polyether may be effected by first dissolving the polyether in a suitable volatile solvent and after thoroughly mixing the absorbent with this solution, heating the mixture to drive off the solvent. Solvents which may be used are water and the lower aliphatic alcohols, preferably ethanol or isopropanol, although any other solvent could be used which is sufficiently volatile to permit its ready removal after admixture with the absorbent material. However, in the case of water it is necessary to use generally larger amounts of the polyether to ensure that after treatment there is enough present on the surface of the particles of the absorbent to enhance blood wet-out. It may be possible to produce the surface-treated absorbent by adding the polyether in solution in a solvent during the process of manufacturing the absorbent. For example, in the case of the absorbent described in German Patent Application No. 2 702 781, the starch derivative in its acid form is conveniently mixed with a solution of the polyether in a volatile solvent, and an alkali, e.g. sodium carbonate or ammonium hydroxide, and the mixture heated to obtain as a dry powder the treated starch derivative in the salt form.

The amount of the polyether that is used for the treatment of the absorbent depends on a number of factors. The amount which is sufficient to effect an enhancement of the dispersibility of the absorbent in blood (i.e. the "blood wet-out" of the absorbent) may vary with the chemical type of absorbent and its physical form, e.g. particle size, and the type and molecular weight of the polyether used in the treatment, as well as on the method of treatment. In general, for a given absorbent, increasing amounts of polyether are required as the molecular weight of the polyether employed increases. It should be noted, however, that excessive amounts of the polyether or polyether mixture inhibit blood dispersibility by preventing capillary flow of blood through a mass of the particulate absorbent. It is required that the blood should be able to percolate through the capillaries or spaces between the particles and therefore these should not be blocked by the polyether. If this occurs the blood would be forced to travel through the mass by diffusion alone: this is a relatively slow process and corresponds to very poor blood wet-out properties. Consequently, the amount of the polyether used for the treatment of the absorbent should not be such as to result in, for example, a mixture having a paste-like or ointment-like consistency such as is produced by the composition described in Example 6 of British Patent Specification No. 1,454,055 (Pharmacia AB).

Employing the gelatinised starch derivatives described in German Patent Application No. 2 702 781 good results have been obtained using as little as 1% by weight of a polyethylene glycol having an average molecular weight of 400 based on the weight of absorbent while amounts of this polyether, when mixed directly with the absorbent, above about 40% should not be used to avoid producing an unsatisfactory ointment-like or pasty mixture. The higher molecular weight, normally solid, polyethylene glycols are generally required to be used in greater amounts than the liquid glycols. For most absorbent materials the amount of polyethylene glycol will not normally be required to exceed about 30% by weight of the absorbent polymer when the direct method of mixing with the absorbent is employed.

The polypropylene glycols and the polyoxyethylenepolyoxypropylene copolymers will generally be used in amounts of from about 1% to about 35% by weight, depending on their molecular weight and the nature of the absorbent. The normally solid copolymers, having generally higher molecular weights, when used alone tend to be required to be used in relatively substantial amounts, e.g. about 25% to about 35% by weight of the absorbent, but again the amount of the polyether required will be dependent to some extent on the chemical type and physical form of the absorbent being treated. As will be shown hereinafter, in certain cases amounts of polyether up to about 50% by weight of the absorbent can be used while still permitting capillary flow of blood through a mass of the particulate treated absorbent.

By treatment of an absorbent with a polyether in accordance with the invention one can also improve the feel to the touch of a mass of absorbent swollen with blood. Many absorbent polymers become very sticky to the touch when blood is added to a mass of the particles. We have found that treatment with the polyether reduces this stickiness.

The treatments described do not markedly affect the blood retention value of an absorbent.

The invention also relates to liquid absorbent articles containing the absorbent material of the invention. The liquid absorbent article may comprise a fibrous carrier or support for the absorbent material, such as a woven or unwoven material such as cotton cloth, rayon, wool, surgical gauze or paper as well as cellulosic fluff, on or within which the absorbent material is supported. The absorbent material may be spread on the carrier or it may be mixed with loose fibres to make a composite fluff or wadding which can be enclosed between cover sheets of paper or cloth. The article may also be in the form of a laminate. In a particular form, the carrier comprises two sheets between which the absorbent material is sandwiched. The absorbent materials of the invention are particularly suitable for use in sanitary towels, napkins or tampons. The production of an absorbent article utilising a particulate absorbent material is described for example in German Patent Application No. 2,702,781.

The invention will now be illustrated by the following examples. Percentages are by weight.

References herein to the "dry-off" of an absorbent refer to feel of the polymer to the touch after a mass of particles of the absorbent has absorbed blood. An absorbent with poor dry-off would be sticky to the touch whereas one with a good dry-off would feel substantially dry and non-sticky. Water and urine retention values are given to the nearest quarter of a unit.

EXAMPLES 1 TO 9

Potato starch (1,000 g) was slurried in water (950 ml) containing epichlorhydrin (8.4 ml.; 1.0% epichlorhydrin by weight of starch). Sodium hydroxide (5 g) in water (50 ml) was added with stirring and the mixture was applied to a heated roller via a feeder roller to form a layer on the surface of the roller of about 0.5 mm thickness. The roller itself was heated using steam at 3.77 bars (140° C.). The cross-linked starch derivative was removed from the roller as a flake material to yield 914 g of product. The soluble content of the product was found to be 25.0 mg/g and the product was found to have a bed volume of 13.5 ml/g. Since about half of the epichlorhydrin was lost by evaporation from the heated roller the degree of substitution of the cross-linking groups was about 0.01.

Sodium hydroxide (34 g) in water (66 ml) followed by monochloracetic acid (39 g) in water (11 ml) was slowly added with stirring to the cross-linked potato starch (100 g) as prepared above. The mixture was aged overnight in a polythene bag. The theoretical degree of substitution was 0.67.

The moist carboxymethyl derivative was dispersed in 10 times its weight of 1N hydrochloric acid and soaked for 15 minutes and then filtered. The gel cake was repeatedly dispersed in water and filtered until the filtrate was substantially free of chloride ions. Ammonium hydroxide, specific gravity 0.910 (70 ml) was mixed with the waterswollen washed cake before drying in a forced air oven (70° C.) and milling (2 mm screen). The milled product has a water retention value of 20.00 g/g, a urine retention value of 10.25 g/g, a solubility of 0.3% and a bed volume of 51 ml/g.

Various polyethylene glycols were used to treat the control material prepared as described above. In the case of the liquid polyethylene glycols in Examples 1 to 5 these were added to the absorbent with thorough mixing. For the normally solid polyethylene glycols used in Examples 6 to 9, these were melted in a glass dish and the control absorbent material mixed with the molten polyether whilst maintaining the mixture just above the melting point of the polyether. The percentages of the polyethylene glycols added which are given in Table I are based on the weight of the control material. In each case the treated absorbent was of particulate form.

TABLE I

| Example | Polyethylene Glycol Molecular Weight | % Added |
|---|---|---|
| 1 | 300 | 5 |
| 2 | 300 | 10 |
| 3 | 400 | 1 |
| 4 | 400 | 5 |
| 5 | 400 | 10 |
| 6 | 600 | 5 |
| 7 | 1,000 | 5 |
| 8 | 1,500 | 10 |
| 9 | 4,000 | 10 |

The products of Examples 1 to 9 each showed a marked improvement in blood wet-out and dry-off compared to the control material to which no addition had been made.

The ability of an absorbent to be wet-out by blood was assessed by placing 1–2 g of the absorbent to be treated on a watch glass and adding to it 1–3 ml of blood. In the cases where the absorbent had been treated with a polyethylene glycol the blood rapidly penetrated the mass of particles whereas in the case of the control material the blood only very slowly, if at all, penetrated the mass to reach the particles in the interior of the mass.

EXAMPLES 10 TO 16

These examples illustrate the use of a mixture of liquid and solid polyethylene glycols.

A mixture of 2 parts by weight of a solid polyethylene glycol of molecular weight 1,500 and 1 part by weight of a liquid polyethylene glycol of molecular weight 400 was heated to just melt the solid component. Various amounts of the control absorbent material as described above with reference to Examples 1 to 9 were thoroughly mixed with the liquid mixture of polyethers.

The percentages of the polyether mixture based on the weight of the control absorbent are given below in Table II.

TABLE II

| Example | % Polyether Mixture |
|---|---|
| 10 | 5 |
| 11 | 9 |
| 12 | 17 |
| 13 | 29 |
| 14 | 30 |
| 15 | 37 |
| 16 | 40 |
| Comparative Example A | 50 |
| Comparative Example B | 60 |

In the case of each of Examples 10 to 16 the treated polymer, which was in particulate form, had a fast blood wet-out. In the case of Comparative Examples A and B, these mixtures did not absorb blood, the amount of polyether being so great in these cases that capillary flow of blood between particles of the absorbent was prevent. The mixture of polyether and absorbent in the case of each of Comparative Examples A and B was not particulate but rather was a continuous ointment-like mass.

EXAMPLES 17 AND 18

Polypropylene glycol, MW 2,025, was added directly, with thorough mixing, to the control absorbent material as described above with reference to Examples 1 to 9. In the case of Example 17 the amount was 6% and in the case of Example 18 10%, both percentages being by weight of the unmodified control material. In both cases the blood wetout and dry-off of the absorbent was improved compared to the unmodified absorbent.

EXAMPLES 19 TO 25

Various water-soluble polyoxyethylene-polyoxypropylene copolymers were mixed with the control absorbent material as described above with reference to Examples 1 to 9. Details of the copolymers used are given in Table III. The copolymers employed in Examples 19 to 24 were liquids and that employed in Example 25 was a solid.

TABLE III

| | Polyoxyethylene-polyoxypropylene copolymer | | | |
|---|---|---|---|---|
| Example | Type | Molecular Weight | Molecular Weight Polyoxypropylene block | % Added |
| 19 | PLURONIC L62 | 2,500 | 1,750 | 10 |
| 20 | PLURONIC L42 | 1,630 | 1,200 | 10 |
| 21 | PLURONIC L43 | 1,850 | 1,200 | 10 |
| 22 | PLURONIC L44 | 2,200 | 1,200 | 10 |
| 23 | PLURONIC L35 | 1,900 | 950 | 5 |
| 24 | PLURONIC L92 | 3,650 | 2,750 | 30 |
| 25 | PLURONIC F38 | 5,000 | 950 | 30 |

The particulate products of Examples 19 to 25 each showed a marked improvement in blood wet-out and dry-off compared to the control material to which no addition had been made.

EXAMPLE 26 TO 28

These examples illustrate the treatment of an absorbent with a solution of a water-soluble polyether.

A solution of a polyether in a solvent was added to the washed cake prior to the addition of ammonium hydroxide in the preparative procedure described above with reference to Examples 1 to 9.

The polyethers and solvents employed together with the percentage weight of the polyether based on the weight of the dry untreated absorbent are given below in Table IV.

TABLE IV

| Example | Polyether | Solvent | % Polyether |
|---|---|---|---|
| 26 | Polyethylene glycol MW 400 | Water | 30 |
| 27 | Polyethylene glycol MW 1,500 | Water | 50 |
| 28 | PLURONIC L43 | Isopropanol | 8 |

The treated products, like the untreated product, were obtained as a powder. They had in each case improved blood wet-out and dry-off properties compared to the untreated absorbent.

EXAMPLES 29 AND 30

The preparation described in Examples 1 to 9 was repeated as far as the production of the washed acid cake which was divided into three equal portions. Polypropylene glycol, molecular weight 2,025, dissolved in isopropanol (20 ml) was added to a portion (238 g) of the washed acid cake. Ammonium hydroxide, specific gravity 0.910, (25 mls) was then mixed in before drying in a forced air oven (70° C.) and milling (2 mm screen).

The amount of polypropylene glycol added expressed as a percentage of the weight of a dried control product to which no polypropylene glycol was added, together with the water and urine retention values of the resultant products and of the control product are given in Table V.

TABLE V

| Example | % Polypropylene Glycol | Water Retention Value (g/g) | Urine Retention Value (g/g) |
|---|---|---|---|
| 29 | 14 | 22.25 | 8.75 |
| 30 | 21 | 17.75 | 7.50 |
| Control | 0 | 17.50 | 9.25 |

The particulate materials of Examples 29 and 30 had much better blood wet-out than the particulate control material containing no polypropylene glycol. The treated absorbents of Examples 29 and 30 also showed a good dry-off whereas blood formed a sticky matt when added to the control material.

EXAMPLES 31 TO 39

Washed acid cake was prepared as described in Examples 1 to 9. A range of polyether materials was added as described in Table VI in the stated percentage based on the weight of the dried control material. The polyethers were dissolved in isopropanol to aid their admixture with the absorbent, prior to ammoniation.

TABLE VI

| Example | Additive | % |
|---|---|---|
| 31 | Polypropylene glycol, MW 400 | 1 |
| 32 | Polypropylene glycol, MW 400 | 5 |
| 33 | Polypropylene glycol, MW 400 | 9 |
| 34 | Polypropylene glycol, MW 1,025 | 7 |
| 35 | Polypropylene glycol, MW 2,025 | 7 |
| 36 | Pluronic L61, MW 2,000 | 6 |
| 37 | Pluronic L81, MW 2,750 | 7 |
| 38 | Pluronic L101, MW 3,800 | 5 |
| 39 | Pluronic L121, MW 4,400 | 7 |

The Pluronic materials used in Examples 36 to 39 are water-insoluble polyoxyethylene polyoxypropylene block copolymers of the formula $HO(C_2H_4O)_a(C_3H_6O)_b(C_2H_4O)_cH$ where in each case a+c is such that the total weight of the polyoxyethylene units is about 10% by weight of the total compound and b is such that the molecular weights of the polyoxypropylene units for the grades L61, L81, L101 and L121 are about 1,750, 2,250, 3,250 and 4,000 respectively.

The particulate products obtained from Examples 31 to 39 showed a marked improvement in blood wet-out and dry-off compared to the control material containing no additive.

EXAMPLE 40

Example 1 was repeated as far as the preparation of the washed acid cake. Polypropylene glycol, MW 2,025 (6 g) dissolved in isopropanol (20 ml) was mixed into the acid cake (800 g). A solution of sodium carbonate (16.2 g) in water (100 ml) was added before drying in a forced air oven (70° C.) and milling (2 mm screen).

The particulate product obtained had improved blood wet-out and dry-off compared to a control material containing no additive. The product had a water retention value of 19.50 g/g and a urine retention value of 9.75 g/g. The corresponding values for the control material were 22.50 g/g and 10.75 g/g.

EXAMPLES 41 TO 44

Polyethylene glycol, molecular weight 400, was added directly with thorough mixing to absorbent materials as described in Table VII each of which had a water retention value greater than 2 g/g. In each case the blood wet-out and dry-off of the absorbent was improved compared to the respective unmodified absorbent.

TABLE VII

| Example | Absorbent | % Polyethylene glycol, MW 400 |
|---|---|---|
| 41 | Absorbent A | 5 |
| 42 | Absorbent B | 30 |
| 43 | Absorbent C | 30 |
| 44 | Absorbent D | 3 |

Absorbent A was the potassium salt of a polyacrylic acid cross-linked by aluminum ions available commercially from National Starch Corporation under the trade name Permasorb and generally described in German Patent Application No. 2609144.

Absorbent B was a carboxymethylated cellulose crosslinked by intermolecular esterification and available from Hercules Corporation under the trade name SPX 1154 and generally described by Podlas, T.J. in INDA Tech. Symp. 1976, 2–3 March, pp 25–39. It is a particulate fibrous material.

Absorbent C was a hydrolysed starch-polyacrylonitrile graft copolymer available from the Grain Processing Corporation under the trade name Polymer 35-A-100 and generally described in U.S. Pat. No. 3,661,815.

Absorbent D was a starch-polyacrylonitrile graft copolymer prepared in accordance with the process described in U.S. Pat. No. 3,981,100.

In the case of Examples 42 and 43 the polyethylene glycol causes some agglomeration of the particles.

EXAMPLES 45 TO 56

The liquid polyoxyethylene-polyoxypropylene block copolymers commercially available under the trade names PLURONIC L42 and PLURONIC L81 were added with thorough mixing to absorbent materials as identified in Tables VIII and IX each of which had a water retention value greater than 2 g/g. The percentage of the copolymers added is based on the weight of the untreated absorbent. In each case the blood wet-out was improved compared to the untreated material.

TABLE VIII

| Example | Absorbent | % PLURONIC L42 |
|---|---|---|
| 45 | A | 26 |
| 46 | B | 30 |
| 47 | C | 35 |
| 48 | D | 4 |
| 49 | E | 7 |
| 50 | F | 40 |

TABLE IX

| Example | Absorbent | % PLURONIC L81 |
|---|---|---|
| 51 | A | 25 |
| 52 | B | 30 |
| 53 | C | 35 |
| 54 | D | 3 |
| 55 | E | 7 |
| 56 | F | 40 |

Absorbent E was a carboxymethylated cellulose crosslinked by intermolecular esterification and available commercially from Hercules Corporation under the trade name Aqualon R and generally described in the article by Podlas, T.J. referred to above.

Absorbent F was a hydrolysed starch-polyacrylonitrile graft copolymer available from General Mills Inc., under the trade name SGP-502S and generally described in U.S. Pat. No. 3,997,484.

EXAMPLES 57 To 61

Polypropylene glycol, MW 2,025, was added directly, with thorough mixing, to absorbent materials as described in Table X. In all cases the blood wet-out and dry-off of the particulate treated absorbents was improved compared to the unmodified absorbents.

TABLE X

| Example | Absorbent | % Polypropylene glycol |
|---|---|---|
| 57 | A | 25 |
| 58 | B | 30 |
| 59 | C | 34 |
| 60 | E | 6 |
| 61 | F | 40 |

Comparative Example C

A cross-linked dextran having a water retention value of about 2.5 g/g was employed to make a product in accordance with Example 6 of British Patent Specification No. 1,454,055 (Pharmacia AB) and having the following composition:

| | % |
|---|---|
| Polyethylene glycol MW 400 | 14.3 |
| Polyethylene glycol MW 1,500 | 28.6 |
| Cross-linked dextran (Sephadex G-25) | 57.1 |

The two polyethylene glycol products were first heated together to form a melt to which dry particles of the crosslinked dextran were added with stirring. The mixture was then cooled.

To the mixture, which had the consistency of an ointment, drops of blood were added. The mixture absorbed blood very slowly, the rate being diffusion controlled. It did not swell or show dry-off properties. The polyethylene glycol mixture is present in such amount that the interparticle pores are blocked preventing capillary flow of the blood between the particles.

What is claimed is:

1. A water-swellable particulate absorbant material surface-treated to enhance its dispersibility in blood with an effective amount of at least one polyether selected from the group consisting of polyoxyethylenes, polyoxypropylenes and polyoxyethylene-polyoxypropylene block copolymers, said effective amount of polyether being such as to permit capillary flow of blood through a mass of the particulate absorbent; wherein:
   (a) said water-swellable particulate absorbent material has a water retention value of at least 2 g/g; and
   (b) said polyether has a molecular weight of about 300 to about 6,000.

2. An absorbent material as claimed in claim 1, wherein the polyether is a liquid.

3. A method of treating a water-swellable particulate absorbent material to enhance its dispersibility in blood comprising contacting the particulate absorbent material with an effective amount of at least one polyether selected from the group consisting of polyoxyethylenes, polyoxypropylenes and polyoxyethylene-polyoxypropylene block copolymers so as to form a coating of polyether on the surface of the particulate absorbent, said effective amount of polyether employed in the treatment being such as to permit capillary flow of blood through a mass of the treated particulate absorbent; wherein:
   (a) said water-swellable particulate absorbent material has a water retention value of at least 2 g/g; and
   (b) said polyether has a molecular weight of about 300 to about 6,000.

4. A method as claimed in claim 3 comprising intimately mixing the particulate absorbent material with at least one liquid or liquefied polyether.

5. A method as claimed in claim 3 comprising intimately mixing the particulate absorbent material with a solution of the polyether in a volatile solvent and then removing the solvent.

6. A method as claimed in claim 5, wherein the volatile solvent is selected from the group consisting of water and the lower $C_2$-$C_4$ aliphatic alcohols.

7. A method as claimed in claim 4, wherein the absorbent material is mixed with from 1 to 40% by weight of the absorbent material of a polyoxyethylene having a molecular weight of from about 300 to about 6,000.

8. A method as claimed in claim 4, wherein the absorbent material is mixed with from 1 to 35% by weight of the absorbent material with a liquid polyoxypropylene having a molecular weight of from about 400 to about 2,500.

9. A method as claimed in claim 4, wherein the absorbent material is mixed with from 1 to 35% by weight of the absorbent material with a liquid or liquefied polyoxyethylenepolyoxypropylene block copolymer having a molecular weight of from about 1,000 to about 6,000.

10. A method as claimed in claim 6 comprising (1) mixing the absorbent material with a solution of the polyether in an alcohol selected from the group consisting of ethanol and isopropanol, said solution containing from 1 to 35% by weight of the polyether based on the weight of the absorbent material, and said polyether having a molecular weight of from about 300 to about 6,000; and (2) removing the alcohol.

* * * * *